United States Patent [19]

Kato et al.

[11] 4,242,528
[45] Dec. 30, 1980

[54] PROCESS FOR PREPARING ISOPROPENYL PHENOL

[75] Inventors: Nobukatu Kato, Tokai; Tsutomu Takase, Nagoya; Yoshio Morimoto, Tokai; Teruo Yuasa; Minoru Hattori, both of Nagoya, all of Japan

[73] Assignee: Mitsui Toatsu Chemicals, Incorporated, Tokyo, Japan

[21] Appl. No.: 62,811

[22] Filed: Aug. 1, 1979

[30] Foreign Application Priority Data

Aug. 15, 1978 [JP] Japan .................. 53-98721

[51] Int. Cl.$^3$ .............................................. C07C 39/06
[52] U.S. Cl. .................................. 568/781; 568/806
[58] Field of Search ............... 568/781, 805, 724, 806, 568/782

[56] References Cited

U.S. PATENT DOCUMENTS

| | | | |
|---|---|---|---|
| 1,798,813 | 3/1931 | Schoeller et al. | 568/781 |
| 4,054,611 | 10/1977 | Mimaki et al. | 568/781 |
| 4,131,749 | 12/1978 | Kiedik et al. | 568/781 |

FOREIGN PATENT DOCUMENTS

| | | | |
|---|---|---|---|
| 660173 | 3/1963 | Canada | 568/781 |
| 905994 | 9/1962 | United Kingdom | 568/781 |
| 303314 | 6/1971 | U.S.S.R. | 568/781 |

OTHER PUBLICATIONS

Derwent Belgium Patent Report Belgian 593, 367, vol. 74A, Mar. 30, 1961, p. C11.

*Primary Examiner*—Werren B. Lone
*Attorney, Agent, or Firm*—Sherman & Shalloway

[57] ABSTRACT

A novel process for producing isopropenyl phenol such as p-isopropenyl phenol which comprises continuously feeding oligomers of isopropenyl phenol having a degree of polymerization of 2 to 5 into a high-boiling inert organic reaction medium such as an alkylnaphthalene heated at 150° to 250° C. under a pressure of 10 to 100 mmHg while maintaining the concentration of the oligomers in the reaction medium at not more than 30% by weight, thereby thermally decomposing the oligomers in the reaction medium; and continuously distilling off the resulting isopropenyl phenol out of the reaction system and recovering it. The process almost quantitatively gives isopropenyl phenol having reduced contents of impurities.

12 Claims, No Drawings

PROCESS FOR PREPARING ISOPROPENYL PHENOL

This invention relates to a process for producing isopropenyl phenol by thermally decomposing oligomers of isopropenyl phenol in an inert organic reaction medium.

It has long been known that isopropenyl phenol is formed by heating oligomers of isopropenyl phenol expressed by the following formula (I) and/or (II)

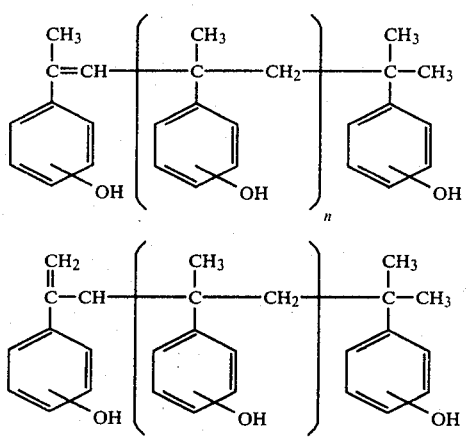

wherein n is an integer of 0 to 3,
to a high temperature. Various methods have been suggested in the past for the production of isopropenyl phenol by thermally decomposing the oligomers of isopropenyl phenol under reduced pressure and distilling off the decomposition product out of the reaction system.

In any of these prior methods, the oligomers of isopropenyl phenol are heated without using a reaction medium, and are thereby thermally decomposed while they are in the molten and liquefied state. Thermal decomposition of isopropenyl phenol oligomers to produce isopropenyl phenol, however, requires latent heat of evaporation for vaporizing the decomposition product in addition to a depolymerization energy. Since the amount of energy thus required is extremely large, it is difficult for any of the prior methods to supply sufficient energy and to distill the decomposition product rapidly out of the reaction system. When the isopropenyl phenol oligomers are directly liquefied and thermally decomposed, the concentration of the undecomposed oligomers in the reaction system is high. Hence, a part of them is distilled off together with the decomposition product, and this tends to decrease the purity of the product. Or side-reactions, such as dealkylation of isopropenyl phenol or conversion of the starting material and/or the decomposition product into a resin owing to localized overheating, take place to decrease the yield of the desired product. Moreover, the side-reaction products may get mixed with the final desired product to reduce its purity.

Accordingly, many difficulties are encountered in the commercial practice of the production of isopropenyl phenol by the thermal decomposition of oligomers of isopropenyl phenol despite the fact that various methods for it have been suggested and its theory has been well known.

It is an object of this invention to provide a process for producing isopropenyl phenol which can be easily practiced commercially, and which gives a solution to the aforesaid problems associated with the production of isopropenyl phenol by the thermal decomposition of oligomers isopropenyl phenol.

The above object of this invention is achieved by a process for producing isopropenyl phenol by the thermal decomposition of oligomers of isopropenyl phenol, which comprises continuously feeding said oligomers into an inert organic reaction medium heated under reduced pressure, at such a rate that the concentration of said oligomers in the reaction medium is maintained at not more than 30% by weight, thereby thermally decomposing said oligomers in said reaction medium; and distilling off the resulting isopropenyl phenol continuously out of the reaction system and recovering it.

The oligomers of isopropenyl phenol used in the process of this invention are compounds of the above formula (I) and/or (II). These compounds are obtained, for example, by thermally cleaving dihydroxydiphenyl propane under reduced pressure in the presence of a basic catalyst, distilling off the resulting isopropenyl phenol and phenol out of the reaction system, and distilling the distillates under reduced pressure to distill off the phenol, whereupon isopropenyl phenol polymerizes to oligomers. The oligomers (I) and/or (II) are obtained as distillation bottoms. When isopropenyl phenol is, for example, p-isopropenyl phenol, the oligomers of isopropenyl phenol are usually composed mainly of 4-methyl-2,4-bis(p-hydroxyphenyl)-pent-1-ene and 4-methyl-2,4-bis(p-hydroxyphenyl)-pent-2-ene which are dimers, but they may contain trimers or tetramers without any deleterious effect. They can be used satisfactorily even when containing some amounts of further impurities such as phenol, dihydroxydiphenylpropane and high-boiling substances.

To decompose the isopropenyl phenol oligomers thermally in the process of this invention, it is necessary to heat the inert organic reaction medium to a temperature sufficient for the smooth decomposition of the isopropenyl phenol oligomers to isopropenyl phenol. Usually, this temperature is preferably in the range of 150° to 250° C. When the temperature of the inert organic reaction medium is lower than 150° C., the thermal decomposition of the isopropenyl phenol oligomers is markedly retarded to prolong the thermal decomposition period, and the rate of distillation of the decomposition product out of the reaction system is decreased. Moreover, a part of the isopropenyl phenol oligomers is distilled in the undecomposed state and gets mixed with the decomposition product to reduce its purity. When the temperature of the inert organic reaction medium is higher than 250° C., side-reactions, such as dealkylation of the resulting isopropenyl phenol or conversion of the starting material and/or the decomposition product into a resin, tend to take place, and therefore, the yield and purity of the product are reduced. Temperatures of 200° to 240° C. are especially preferred because within this temperature range, the formation of by-products is reduced, and the decomposition proceeds smoothly.

After the formation of the thermal decomposition product, it must be distilled off out of the reaction system rapidly. For this purpose, the thermal decomposition reaction system or the inert organic reaction medium must be maintained at reduced pressure. The degree of pressure reduction varies depending upon the thermal decomposition temperature, but usually, a range of 10 to 100 mmHg is suitable. When the pressure is lower than 10 mmHg, a part of the isopropenyl phenol oligomers or a part of the inert organic reaction medium is distilled together with the thermal decomposition product and gets mixed with the product, thus decreasing the purity of the product. When the pressure is higher than 100 mmHg, it is difficult to distill the thermal decomposition product out of the reaction system. This naturally prolongs the residence time of the product in the reaction system, and side-reactions, such as conversion of isopropenyl phenol into a resin or its dealkylation, are liable to occur. As a result, the yield is decreased, and the purity of the product is decreased with the inclusion of the by-products in the desired product. To perform the reaction smoothly by rapidly distilling off the thermal decomposition product out of the reaction system, the pressure is preferably 50 to 100 mmHg, especially preferably 50 to 70 mmHg.

To thermally decompose the oligomers of isopropenyl phenol at the aforesaid temperature and pressure, the inert organic reaction medium is suitably a high-boiling inert organic solvent which has a melting or softening point of not more than 150° C. and a lower vapor pressure than the vapor pressure of the resulting isopropenyl phenol at the thermal decomposition temperature of the oligomers of isopropenyl phenol. More specifically, high-boiling inert organic solvents having a vapor pressure at 250° C. of not more than 100 mmHg are suitable. Examples of these organic solvents are hydrocarbon type heat transfer media such as alkyl-naphthalenes (KSK-Oil and Neo SK-Oil are available as commercial products made by Souken Kagaku Co. Inc.); high-boiling substances formed as by-products in a condensation reaction between phenols and ketones, for example, the residues of a distillation tower or extraction tower which are left after separation of bisphenol A by distillation or extraction from the reaction product of phenol and acetone in the production of bisphenol A (to be referred to as bisphenol A distillation residue); and novolak-type phenolic resins having a softening point, determined by JIS K-2531 (JIS denotes Japanese Industrial Standards), of 60° to 150° C. obtained by condensing formaldehyde with an excess of phenol or cresol in the presence of an acid.

The inert organic reaction medium used in this invention must well dissolve the isopropenyl phenol oligomers at 150° to 250° C. The above-exemplified reaction media meet this requirement.

Thermal decomposition of the oligomers of isopropenyl phenol in the process of this invention is effected by feeding the reaction medium into a reactor equipped with a feed inlet for the starting oligomers of isopropenyl phenol, a distillation outlet for isopropenyl phenol as a thermal decomposition product, a thermometer and optionally a stirring (mixing) device, maintaining the reaction medium at a high temperature of preferably 150° to 250° C. and a pressure of preferably 10 to 100 mmHg, and feeding the starting oligomers of isopropenyl phenol into the reactor. The isopropenyl phenol oligomers so fed dissolve in the reaction medium, and are thermally decomposed to isopropenylphenol in the liquid phase. The decomposition product is vaporized and distilled off rapidly out of the reaction system. In the above operation, it is essential that the isopropenyl phenol oligomers should be continuously fed into the reactor at such a rate that the concentration of the oligomers in the reaction medium is maintained at not more than 30% by weight. If the isopropenyl phenol oligomers are fed at such a high rate that the oligomer concentration exceeds 30% by weight, supplying of the amount of heat sufficient for the distillation of the decomposition product becomes difficult in the above thermal decomposition reaction which requires such a large amount of energy. As a result, the amount of the thermal decomposition product that builds up in the reaction system increases and its conversion to a resin proceeds to reduce the yield of the desired isopropenyl phenol.

Thermal decomposition of the starting material and the distillation of the decomposition product are especially smooth, and good results are obtained, when the isopropenyl phenol oligomers concentration in the reaction medium is 2 to 15% by weight.

The concentration of the isopropenylphenol oligomers in the reaction medium can be determined by, for example, gas-chromatography.

Stirring (mixing) of the starting material in the reaction medium is possible by an ordinary mechanical method. In the process of this invention, it is especially advantageous to bubble an inert gas such as nitrogen, carbon dioxide, helium or argon through the reaction medium. This results in the stirring and mixing of the reaction medium, and makes the thermal decomposition of the isopropenylphenol oligomers smooth. Moreover, it facilitates the distillation of the resulting isopropenyl phenol out of the reaction system.

The isopropenyl phenol distilled out of the reaction system can be recovered by cooling to condense it into a liquid or solid, or by dissolving it without condensation or immediately after condensation in a high-boiling polar solvent such as 2-ethylhexanol. The isopropenyl phenol so obtained is used as a material for various organic syntheses.

In the present invention, the efficiency of heat transfer increases, and localized overheating can be prevented, by effecting thermal decomposition of the oligomers of isopropenyl phenol in the reaction medium while maintaining the concentration of the oligomers in the reaction medium at not more than 30% by weight. Hence, the thermal decomposition temperature can be easily controlled. Furthermore, the present invention makes it possible to supply a large amount of energy required for the thermal decomposition of the oligomers of isopropenyl phenol and for the distillation of the resulting isopropenyl phenol rapidly out of the reaction system, and therefore, isopropenyl phenol with reduced contents of by-products or impurities can be obtained almost quantitatively.

The following examples illustrate the process of this invention. All percentages in these examples are by weight.

EXAMPLE 1

A reactor (capacity 1 liter) equipped with a feed inlet for a starting material, a distillation outlet for a decomposition product, an inlet tube (bubbling tube) for introduction of an inert gas and a thermometer was charged with 85 g (the depth of liquid 3.1 cm) of KSK-Oil (a product os Souken Kagaku Co. Inc.). KSK-Oil was maintained at a temperature of 240° C., and the inside of the reactor was maintained at a pressure of 50 mmHg. From the feed inlet for starting material, oligomers of p-isopropenyl phenol were continuously fed into KSK-Oil at a rate of 350 g/hr, and a nitrogen gas was introduced at a rate of 4.3 liters/min. from the inlet tube and bubbled through KSK-Oil. As a result, the thermal decomposition product was continuously distilled out of the reactor, cooled, condensed and collected. During the thermal decomposition, the concentration of the p-isopropenyl phenol oligomers in the KSK-Oil was maintained at an average of 10.0%.

The above reaction was performed for 10 hours to decompose 3,500 g of the oligomers of p-isopropenyl phenol. There was obtained 3,430 g (yield 98.0%) of p-isopropenyl phenol having a purity of 94.1%.

The oligomers of p-isopropenyl phenol used as a starting material were produced by a known method (Japanese Patent Publication No. 10869/77). Specifically, bisphenol A was heated under reduced pressure in the presence of a basic catalyst to cleave it. The distillate was condensed to form a mixture of phenol, monomeric p-isopropenyl phenol and linear oligomers of p-isopropenyl phenol. Then, the phenol was almost completely distilled off from the mixture. The residue was heated at 140° C. for 1 hour to afford an oligomeric mixture of p-isopropenyl phenol composed of 83% of dimer, 4.3% of trimer, 2.1% of a tetramer and 0.9% of pentamer.

EXAMPLE 2

The same reactor as described in Example 1 was charged with 80 g (the depth of liquid 2.9 cm) of a bisphenol A distillation residue which was left after separation of bisphenol A by distillation from the reaction product of phenol and acetone in the production of bisphenol A. Under the same conditions as described in Example 1, 3500 g of oligomers of p-isopropenyl phenol were decomposed. The concentration of the p-isopropenyl phenol oligomers in the reaction medium was maintained at 10.5%.

There was obtained 3,470 g (yield 99.1%) of p-isopropenyl phenol having a purity of 93.0%.

EXAMPLE 3

The same reactor as described in Example 1 was charged with 80 g (the depth of liquid 2.9 cm) of a novolak resin having a softening point, determined by JIS K-2531, of 90° C.

Under the same conditions as in Example 1, 3500 g of oligomers of p-isopropenyl phenol were decomposed. During the thermal decomposition, the concentration of the oligomers of p-isopropenyl phenol in the reaction medium was maintained at 10.5%.

There was obtained 3,448 g (yield 98.5%) of p-isopropenyl phenol having a purity of 92.9%.

EXAMPLES 4 to 6

The same reactor as used in Example 1 was charged with 80 g (the depth of liquid 2.9 cm) of a bisphenol A distillation residue which was left after the separation of bisphenol A by distillation from the reaction product of phenol and acetone in the production of bisphenol A. Oligomers of p-isopropenyl phenol were decomposed under the conditions shown in Table 1, in which the thermal decomposition temperature refers to the temperature of the bisphenol A distillation residue, and the thermal decomposition pressure, to the pressure of the inside of the reactor. During the thermal decomposition, nitrogen gas was introduced at a rate of 4.3 liters/min. from the gas inlet tube, and bubbled through the bisphenol A distillation residue.

The yield (g, %) and purity of the resulting p-isopropenyl phenol obtained are shown in Table 2.

Table 1

| Example | Thermal decomposition temperature (°C.) | Thermal decomposition pressure (mm/Hg) | Feed rate of the oligomers (g/hr) | Oligomers concentration in the bisphenol A distillation residue (%) | Thermal decomposition time (hr) | Total amount of the oligomers fed (g) |
|---|---|---|---|---|---|---|
| 4 | 210 | 30 | 300 | 27.0 | 10 | 3,000 |
| 5 | 245 | 70 | 500 | 15.0 | 10 | 5,000 |
| 6 | 250 | 100 | 500 | 5.0 | 10 | 5,000 |

Table 2

| Example | p-Isopropenyl phenol | | |
|---|---|---|---|
| | Yield (g) | Yield (%) | Purity (%) |
| 4 | 2,925 | 97.5 | 95.0 |
| 5 | 4,940 | 98.8 | 92.2 |
| 6 | 4,925 | 98.5 | 92.0 |

COMPARATIVE EXAMPLE 1

The same reactor as described in Example 1 was used, and the inside of the reactor was maintained at a temperature of 240° C. and a pressure of 50 mmHg. Without using a reaction medium, oligomers of p-isopropenyl phenol were fed continuously from the feed inlet at a rate of 350 g/hr for 2 hours and decomposed under the same conditions as in Example 1.

There was obtained 460 g (yield 65.7%) of p-isopropenyl phenol having a purity of 80.2%.

COMPARATIVE EXAMPLE 2

One thousand grams of the oligomers of p-isopropenyl phenol were treated under the same conditions as in Example 1 except that the rate of feeding the oligomers was set at 2,000 g/hr, and the concentration of the oligomers in the reaction medium was maintained at 50%.

There was obtained 571 g (yield 57.1%) of p-isopropenyl phenol having a purity of 78.9%.

What we claim is:

1. A process for producing isopropenyl phenol by the thermal decomposition of oligomers of isopropenyl phenol, which comprises continuously feeding said oligomers into an inert organic reaction medium, said inert organic reaction medium consisting of a high boiling inert organic solvent which has a melting or softening point of not more than 150° C. and a lower vapor pressure than the vapor pressure of the resulting isopropenyl phenol after thermal decomposition temperature of said oligomers of isopropenyl phenol, heating said reaction medium to a temperature of 150° to 250° C., at a pressure of 10 to 100 mmHg, at such a rate that the concentration of said oligomers in the reaction medium is maintained at not more than 30% by weight, thereby thermally decomposing said oligomers in said reaction medium; and distilling off the resulting isopropenyl phenol continuously out of the reaction system and recovering it.

2. The process of claim 1 wherein said inert organic reaction medium is heatd at 150° to 250° C. under 50 to 100 mmHg.

3. The process of claim 1 wherein said inert organic reaction medium is heated at 200° to 240° C. under 50 to 70 mmHg.

4. The process of claim 2 wherein said inert organic reaction medium is a hydrocarbon-type heat transfer medium, a distillation tower residue or extraction tower residue left after the separation of bisphenol A by distillation or extraction from the reaction product of phenol and acetone in the production of bisphenol A, or a novolak-type phenolic resin having a softening point of 60° to 150° C. obtained by condensing formaldehyde with an excess of phenol or cresol in the presence of an acid.

5. The process of claim 4 wherein said oligomers of isopropenyl phenol are continuously fed into the inert organic reaction medium at such a rate that the concentration of said oligomers in the inert organic reaction medium is maintained at 2 to 15% by weight.

6. The process of claim 2 wherein said oligomers of isopropenyl phenol are oligomers of p-isopropenyl phenol.

7. The process of claim 5 wherein said oligomers of isopropenyl phenol are oligomers of p-isopropenyl phenol.

8. The process of claim 1 wherein during the thermal decomposition, said reaction medium is stirred by bubbling an inert gas selected from nitrogen, carbon dioxide, helium and argon through the reaction medium.

9. A process for producing isopropenyl phenol by the thermal decomposition of oligomers of isopropenyl phenol, which consists essentially of continuously feeding said oligomers into an inert organic solvent reaction medium, heating said reaction medium to a temperature of 200° to 240° C., at a pressure of 50 to 70 mmHg, maintaining at least 2% and not more than 30% by weight of said oligomers in the reaction medium, thermally decomposing said oligomers in said reaction medium; and distilling off the resulting isopropenyl phenol continuously out of the reaction system and recovering it.

10. The process of claim 9 wherein said inert organic reaction medium is a high-boiling inert organic solvent which has a melting or softening point of not more than 150° C. and a lower vapor pressure than the vapor pressure of the resulting isopropenyl phenol at the thermal decomposition temperature of said oligomers of isopropenyl phenol.

11. The process of claim 9 wherein said inert organic reaction medium is a hydrocarbon type heat transfer medium, a distillation tower residue or extraction tower residue left after the separation of bisphenol A by distillation or extraction from the reaction product of phenol and acetone in the production of bisphenol A, or a novolak-type phenolic resin having a softening point of 60° to 150° C. obtained by condensing formaldehyde with an excess of phenol or cresol in the presence of an acid.

12. The process of claim 9 wherein during the thermal decomposition, said reaction medium is stirred by bubbling an inert gas selected from nitrogen, carbon dioxide, helium and argon through the reaction medium.

* * * * *